United States Patent [19]

Passafaro et al.

[11] Patent Number: 5,010,886
[45] Date of Patent: Apr. 30, 1991

[54] MEDICAL PROBE ASSEMBLY HAVING COMBINED ULTRASONIC IMAGING AND LASER ABLATION CAPABILITIES

[75] Inventors: James D. Passafaro, Santa Ana; James M. Griffith, Newport Beach, both of Calif.

[73] Assignee: InterTherapy, Inc., Santa Ana, Calif.

[21] Appl. No.: 395,840

[22] Filed: Aug. 18, 1989

[51] Int. Cl.⁵ .............................................. A61B 8/12
[52] U.S. Cl. .......................... 128/660.03; 128/662.06
[58] Field of Search ...................... 128/660.03, 662.06; 606/7, 15

[56] References Cited

U.S. PATENT DOCUMENTS

| | | | |
|---|---|---|---|
| 3,779,234 | 12/1973 | Eggleton et al. | 128/662.06 |
| 3,938,502 | 2/1976 | Bom | 128/662.06 |
| 4,354,502 | 10/1982 | Colley et al. | 128/662.06 |
| 4,576,177 | 3/1986 | Webster, Jr. | 128/660.03 |
| 4,587,972 | 5/1986 | Morantte, Jr. | 128/660.03 |
| 4,641,912 | 2/1987 | Goldenberg | 350/96.10 |
| 4,672,963 | 6/1987 | Barken | 128/303.1 |
| 4,747,405 | 5/1988 | Leckrone | 128/303.1 |
| 4,756,313 | 7/1988 | Terwilliger | 128/662.06 |
| 4,757,821 | 7/1988 | Snyder | 128/662.06 |
| 4,760,845 | 8/1988 | Kovalcheck | 128/303.1 |
| 4,765,330 | 8/1988 | Bach | 128/303.1 |
| 4,785,805 | 11/1988 | Joffe et al. | 128/303.1 |
| 4,785,806 | 11/1988 | Deckelbaum | 128/303.1 |
| 4,794,931 | 1/1989 | Yock | 128/660.03 |
| 4,841,977 | 7/1989 | Griffith et al. | 128/660.03 |
| 4,887,605 | 12/1989 | Angelsen et al. | 606/7 |
| 4,911,173 | 3/1990 | Terwilliger | 128/4 X |

Primary Examiner—Francis Jaworski
Attorney, Agent, or Firm—Nixon & Vanderhye

[57] ABSTRACT

Intravascular probe assemblies are provided with both ultrasonic imaging and laser ablation (angioplasty) capabilities. In preferred embodiments, the probe assemblies will include a distally positioned rotatable housing having an ultrasonic transducer and an optical fiber operatively fixed therein so as to respectively emit acoustic energy and laser radiation along a common path generally parallel to the housing's axis, but in opposing axial directions. An optical and acoustic reflector is interposed between the transducer and optical fiber so as to redirect incident acoustic energy and laser radiation generally radially with respect to the housing.

24 Claims, 5 Drawing Sheets

MEDICAL PROBE ASSEMBLY HAVING COMBINED ULTRASONIC IMAGING AND LASER ABLATION CAPABILITIES

RELATED PATENTS AND APPLICATIONS

This application is related to U.S. Pat. No. 4,899,957 issued on Feb. 13, 1990, Ser. No. 07/395,839 filed on Aug. 18, 1989, the entire content of each said patent and copending application being expressly incorporated hereinto by reference.

FIELD OF INVENTION

The present invention relates generally to diagnostic and therapeutic medical probe assemblies. More specifically, the invention relates to especially adapted intravascular probe assemblies having the dual capabilities of imaging (in real or delayed time) an arterial region of a patient's cardiovascular system using ultrasonic imaging techniques, and therapeutically treating afflictions (e.g., ateriosclerotic plaque) located within the arterial region via laser ablation (angioplasty) techniques. In preferred forms, the invention is embodied in a probe assembly having a distally located housing sized and configured so as to be capable of traversing small sized vessels within a patient's cardiovascular system. The housing includes an angled reflective surface which is positioned axially between a terminal end of an optical fiber and an ultrasonic transducer which respectively emit laser radiation and acoustic energy along directionally opposing axial paths towards the reflective surface within the housing. The reflective surface radially redirects incident acoustic energy and laser radiation so that combined (and simultaneous, if desired) ultrasonic imaging and laser ablation procedures can be accomplished by the attending physician.

BACKGROUND AND SUMMARY OF THE INVENTION

Intravascular probes which include ultrasound imaging crystals are well known. For example, it has previously been proposed to mount a piezoelectric crystal element (conventionally termed a "transducer") on or within a catheter of the type which can be inserted into a blood vessel. Once the probe has been inserted into a blood vessel, the transducer is electro-mechanically excited (as by the application of an electrical signal) to cause emission of ultrasonic energy into the surrounding tissue. While much of the emitted energy is absorbed and scattered by the surrounding tissue, a sufficient amount of energy is reflected back toward the transducer to permit imaging (with reflection occurring principally at the interfaces between different types of biological material, e.g., the interface between blood and the vascular wall, the interface between blood and lesions adhered to the vascular wall etcetera).

The transducer, in turn, produces weak electrical signals in response to electro-mechanical excitation by the returning reflected ("echo") ultrasonic energy. These weak electrical signals can be used to determine the geometry and/or other characteristics of the blood vessel, for example, to determine whether or not the blood vessel contains lesions or other abnormalities. These determinations are usually termed "imaging" since suitable video and/or other signal monitoring equipment are employed to convert the weak electrical signals produced by the transducer into human-readable form. Information gained from such imaging thus may assist the physician in a vascular treatment in real time or in diagnosing a patient's particular ailment or disease so that suitable therapy can be prescribed.

Intravascular imaging through 360° has also been proposed. For example, in the above-referenced U.S. Pat. No. 4,841,977, novel intravascular ultrasonic imaging probes are disclosed having transducer arrays which include radially spaced-apart transducers. These radially spaced apart transducers thereby image corresponding radial segments of the vessel interior under examination (with conventional algorithms being utilized when necessary to "fill in" missing image segments through interpolation and/or partial images to provide sufficient information to a viewer).

It has also recently been proposed in U.S. Pat. No. 4,794,931 to Yock to provide intravascular imaging probes with a stationary transducer and an ultrasonic wave reflector which is rotatable and longitudinally movable relative to the transducer. (See, FIGS. 10 and 11 of Yock '931, and the corresponding description thereof). Moreover, it will be observed that the imaging devices disclosed in Yock '931 are each provided with a forwardly extending guide wire which serves to guide or steer the housing (which includes the transducer and reflection mirror) as the probe is introduced into the vessel of the patient's vascular system.

The use of laser energy as a means of performing surgical procedures is also well known as evidenced by U.S. Pat. Nos. 4,785,805 to Joffe et al; 4,641,912 to Goldenberg; 4,760,845 to Kovalcheck; 4,765,330 to Bach; and 4,785,806 to Deckelbaum. In general, all of these prior art laser surgery devices employ a laser guide as a means for guiding laser energy to a distal portion of the probe, where it is emitted and used to ablate afflicted tissue.

In U.S. Pat. No. 4,672,963 to Barken, a system which employs ultrasonic imaging techniques and laser ablation techniques has been proposed. In the system of Barken '963, however, separate discrete probes respectively dedicated to performing ultrasonic imaging and laser ablation procedures are employed.

Recently, a probe assembly which integrates ultrasonic imaging and laser ablation techniques has been proposed in U.S. Pat. No. 4,576,177 to Webster, Jr. In one embodiment of the probe disclosed in this patent (see FIG. 1), a disc-shaped piezoelectric crystal is positioned at a distal end of a catheter and is disposed at an angle relative to the catheter axis so as to direct ultrasonic signals generated thereby towards the blood vessel wall. An optical fiber extends the length of the catheter and terminates in operative association with a microlens which is said to change the direction of the laser irradiation to about the center of, and in the same general direction as, the transmitted ultrasonic signal (see, column 5, lines 16–30 in Webster, Jr. '177).

In distinct contrast to the probe assemblies of the prior art, the preferred probe assemblies of the present invention direct the ultrasonic imaging waves and laser radiation along an essentially common path, but in opposing axial directions, towards a reflective surface interposed therebetween. The incident ultrasonic waves and laser radiation is therefore redirected generally radially of the probe along respective radial paths. By rotating the operative elements (e.g., the reflective surface and/or the housing which contains it in addition to the terminal end of the optical fiber and the ultrasonic transducer), 360° imaging and laser ablation can be accomplished.

Further aspects and advantages of the present invention will become more clear after careful consideration is given to the detailed description of the preferred exemplary embodiments thereof which follow.

BRIEF DESCRIPTION OF THE ACCOMPANYING DRAWINGS

Reference will hereinafter be made to the accompanying drawings wherein like reference numerals throughout the various FIGURES denote like structural elements, and wherein.

DETAILED DESCRIPTION OF THE PREFERRED EXEMPLARY EMBODIMENTS

Figure 1:
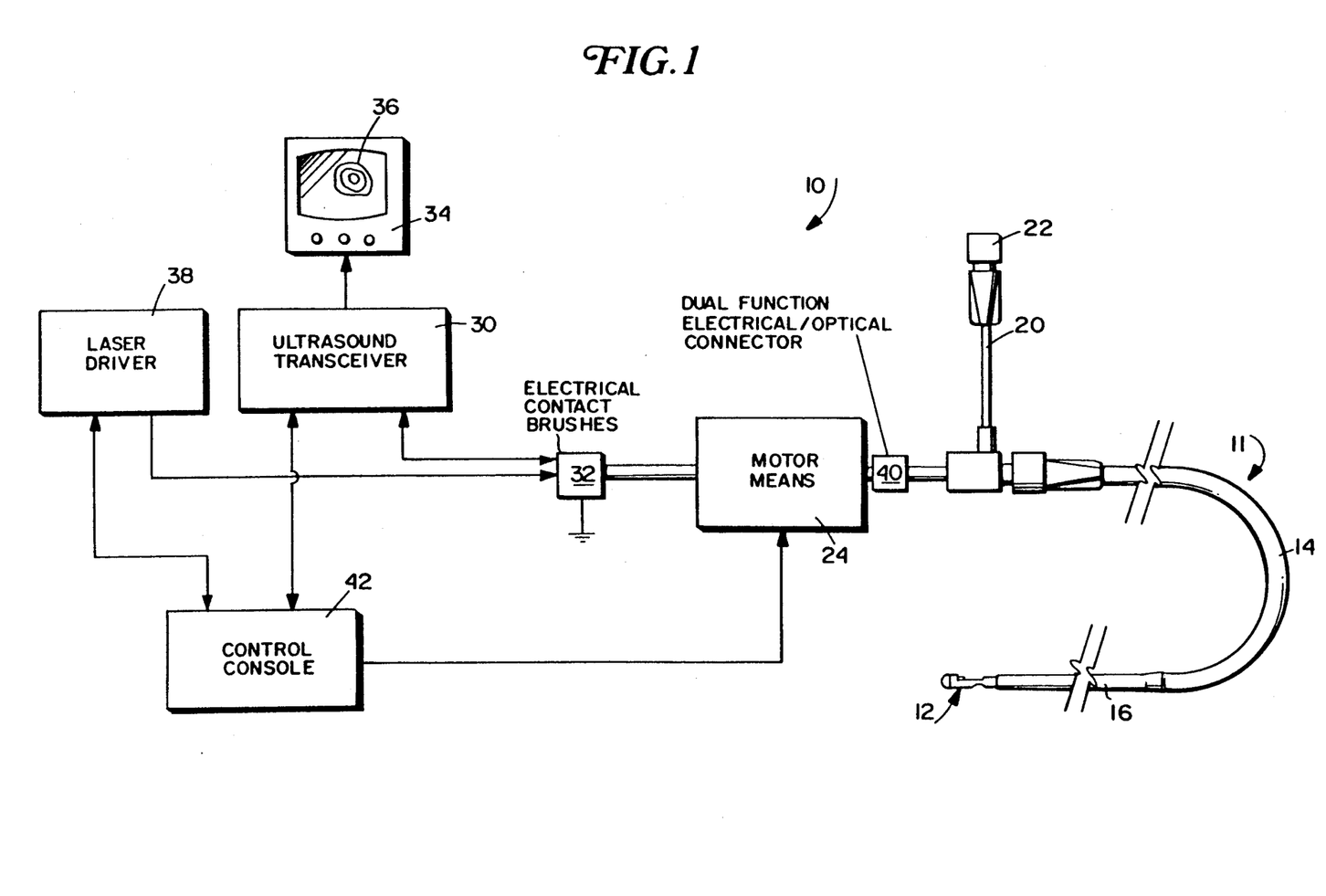
FIG. 1 is a schematic diagram of an exemplary operative ultrasonic imaging and laser angioplasty system with which the probe assembly of this invention is used.

A schematic diagram of an exemplary ultrasound imaging/laser angioplasty system 10 is shown in accompanying FIG. 1. System 10 generally includes a probe assembly 11 having a distal housing subassembly 12 inserted operatively within a guide catheter 14. The distal end of the guide catheter 14 includes a region 16 of reduced wall thickness as compared to the wall thickness of catheter 14 to provide a "window" that is relatively transparent to ultrasonic imaging waves (i.e., is minimally attenuative to and/or reflective of ultrasonic energy), as is more fully described in the above-referenced commonly owned and copending U.S. application Ser. No. 07/395,839.

The proximal (and patient-external) end of the guide catheter 14 is coupled to a conventional side arm connector 20 having a port 22 through which saline solution may be introduced into the lumen 14a (see FIG. 2) of guide catheter 14. The housing 12 is coupled to suitable motor means 24 via structures to be described in greater detail below. Suffice it to say here that the motor means 24 provides the drive for rotating the housing 12 (as may occur during an imaging procedure) and can be any suitable high speed precision motor. Preferably, the motor means 24 is a variable precision motor capable of rotating the housing 12 between zero to about 1800 rpm.

Figure 2:
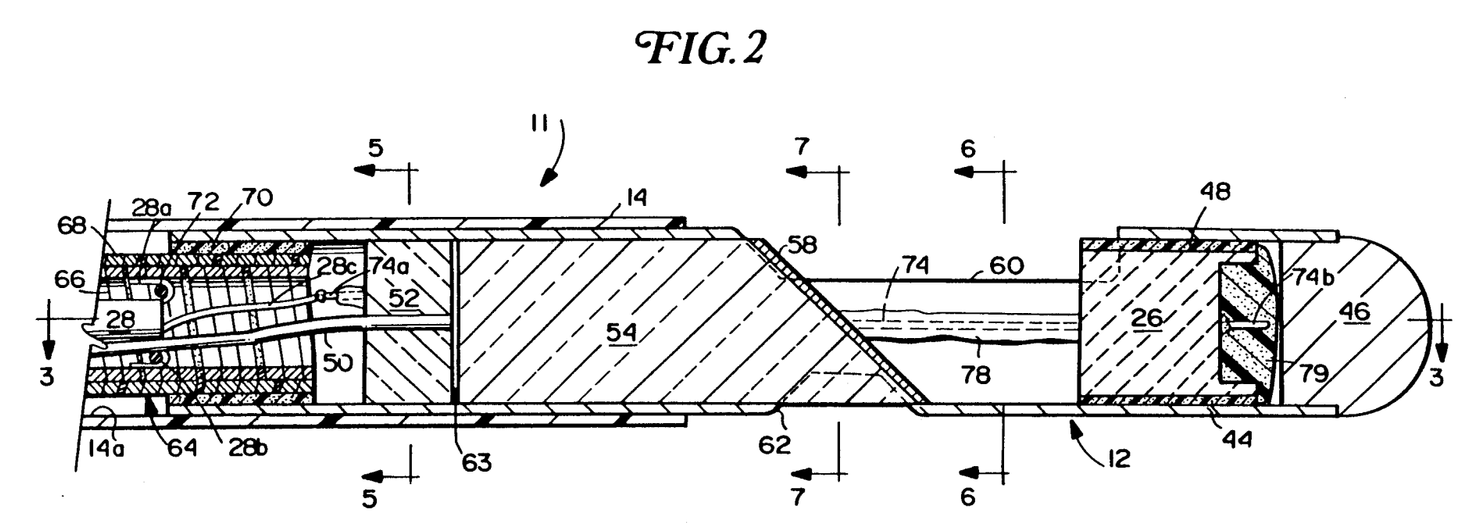
FIG. 2 is a longitudinal cross-sectional side view showing the distal end of the probe assembly of this invention, and more particularly, the operative components within the probe assembly's distally located housing.

Electrical communication with the ultrasonic imaging components within housing 12 (e.g., the electroacoustic transducer 26—see FIG. 2) is provided by a conventional two lead microcoax cable 28 (see also FIG. 2). During an ultrasonic imaging procedure in which the housing 12 rotates in a predetermined rotation direction, electrical communication is established between the electroacoustic transducer 26 (via the microcoax cable 28) and the ultrasound transceiver 30 via suitable electrical contact brushes 32. The ultrasound transceiver 30 produces a pulse signal (of desired magnitude and shape) which is applied via the cable 28 (through brushes 32) to excite the electroacoustic transducer 26 positioned in the distal end of housing 12. The transceiver 30 also performs conventional signal processing operations (e.g., amplification, noise reduction and the like) on electrical signals generated by electromechanical excitation of the transducer 26 within the housing 12 (i.e., signals generated by the transducer in response to receiving echo waves).

These signals are further processed digitally via known display algorithms (e.g., conventional PPI (radar) algorithms) and are then supplied as an input to a CRT monitor 34 (or any other equivalent display device) so as to generate an ultrasound image 36 of desired format representative of the vascular structures reflecting ultrasonic energy toward the transducer 26 within the housing 12.

A laser driver 38 provides a source of laser radiation and supplies a pulse of the same (of desired intensity and duration) via suitable optical guides through contact brushes 30 to a dual function electrical/optical connector 40. The connector 40 serves to operatively couple the electrical and optical components within housing 12 ultimately to the ultrasound transceiver 30 and laser driver 38.

A control console 42 may be employed by the attending physician so as to select the desired operational parameters of the ultrasound transceiver 30 and/or motor means 24 and/or laser driver 38. For example, the console 42 may be employed to select the desired synchronous operation of the ultrasound transceiver 30 and laser driver 38 so as to effect simultaneous operation of the same.

Figure 3:
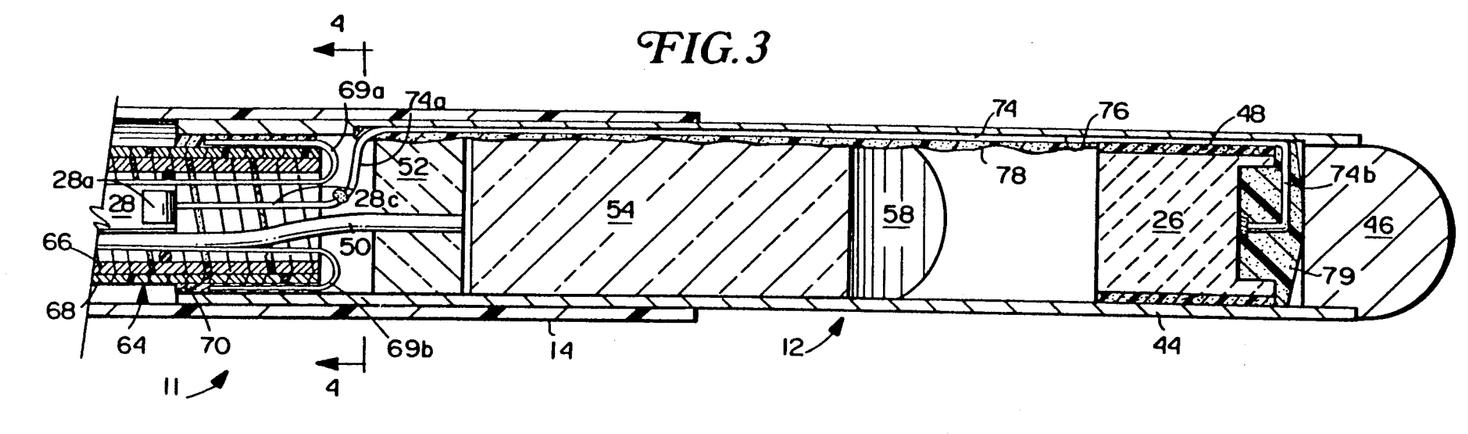
FIG. 3 is a longitudinal cross-sectional top view of the probe assembly's distal end as taken along line 3—3 in FIG. 2.
Figure 4:
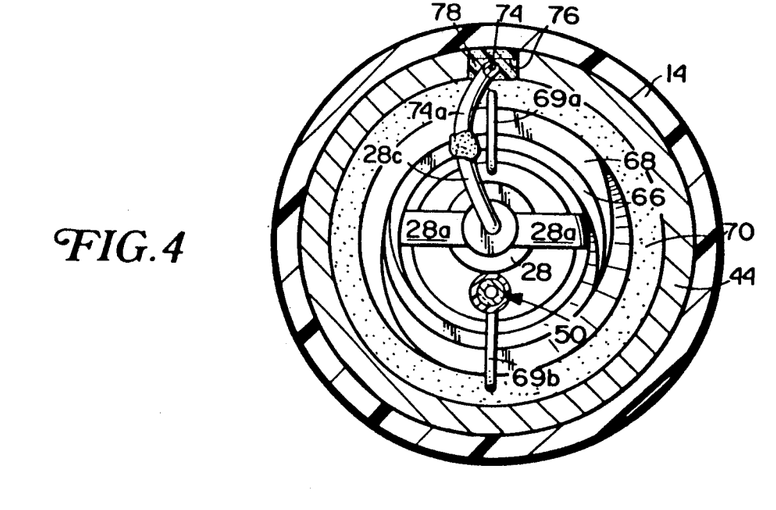
FIG. 4 is a latitudinal cross-section of the probe assembly distal end as taken along line 4—4 in FIG. 3.

The housing 12 and the structures which serve to connect the same electrically, optically, and mechanically to the patient-external environment are shown principally in accompanying FIGS. 2-4. The distal end of the probe assembly 11 according to this invention includes the housing subassembly 12 and is shown in FIGS. 2 and 3 as being extended beyond the distal end of the guide catheter 14 (which is the operative position of the subassembly 12 during laser ablation procedures). The subassembly 12 is, moreover, sized so as to be operatively received within the essentially cylindrical lumen 14a of guide catheter 14. The housing subassembly 12 principally includes a rigid tubular housing 44 which may be fabricated, for example, from conventional stainless steel hypodermic tubes. The distal-most end of housing 44 terminates in a smooth convex tip 46 which is preferably formed of a noble metal (e.g., gold) so that progress and/or positioning of the housing 44 within the patient's cardiovascular system can be perceived visually by the attending physician using conventional fluoroscopic techniques.

The electroacoustic transducer 26 is rigidly affixed within the distal end of housing 44, preferably via an electrically conductive epoxy cement layer identified generally as reference numeral 48 in FIGS. 2 and 3. The preferred electroacoustic transducer 26 will be of the type disclosed in the above-identified U.S. Pat. No. 4,841,977 and/or copending U.S. application Ser. No. 07/395,839. That is, the transducer 26 will be in the form of a cylindrical body of a suitable piezoelectric material which is precision cut so as to resonate at a desired frequency (e.g., about 25 MHz) of operation.

Figure 5:
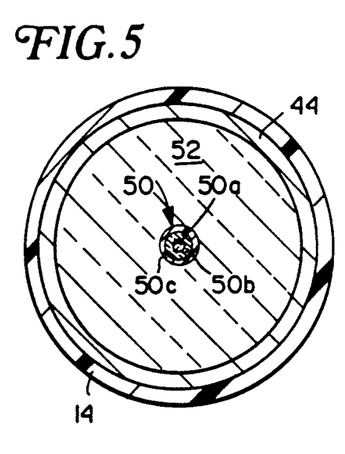
FIG. 5 is a latitudinal cross-sectional view of the probe assembly distal end as taken along line 5—5 in FIG. 2.

An optical fiber 50 extends the entire length of the probe assembly 11 and terminates within the proximal end of the housing 12. The terminal end of the optical fiber 50 is preferably maintained essentially coaxially relative to the longitudinal axis of the housing 12 via a cylindrical ferrule 52 affixed to the housing 12 via suitable epoxy cement. As is perhaps best seen in FIG. 5, the optical fiber 50 is, in and of itself, conventional in that it includes a central core 50a, a cladding layer 50b covering the core 50a, and an outer resin sheath 50c.

A body 54 formed of a suitable material essentially transparent to laser radiation (e.g., clear sapphire) is positioned within the housing 12 between the ferrule 52 (and hence the terminal end of the optical fiber 50) and the transducer 26. The distal end of the body 54 is angled (preferably 45°) and includes a suitable metallized (e.g., aluminum) layer 58 thereon. The layer 58 thus serves to reflect both the laser radiation (emitted by the optical fiber 50 and directed essentially coaxially in a distal direction) and ultrasonic waves (emitted by the transducer 26 and travelling coaxially in a proximal direction) along respective radially directed paths relative to the longitudinal axis of the housing 44.

The housing 44 includes, in this regard, an open trough 60 which allows the radially redirected ultrasonic waves to travel unimpeded towards the tissue being imaged (and to allow the returning echo waves to travel unimpeded towards the reflective layer 58 where they are redirected towards the transducer 26 along the axis of the housing 44). A circumferential window 62 is likewise formed in the housing 44 generally opposite the trough 60 so as to allow the radially redirected laser radiation to pass therethrough and on to the afflicted tissue to be ablated.

It will be observed that, in FIGS. 2 and 3, a small clearance space 63 is defined between the distal face of the ferrule 52 and the proximal face of the body 54, which may be filled with a suitable liquid or gaseous refractive index matching fluid (e.g., air, immersion oils, chlorinated fluorocarbons, and the like) so as to optically couple the laser emitted by the terminal end of the optical fiber 50 to the essentially laser-transparent body 54 so as to minimize reflective losses occurring therebetween. The distal face of ferrule 52 and the proximal face of the body 54 may, however, be in abutting contact with one another, if desired.

A polymer-impregnated torque cable 64 transfers the rotational drive imparted by the proximally (and patient external) motor means 24 to the housing 12. Preferably, the torque cable 64 is formed of inner and outer oppositely helically wound subcables 66, 68, respectively, and is longitudinally stiffened by impregnating a polymer into the interstices between adjacent windings of the subcables 66 and 68. The oppositely wound subcables 66 and 68 are such that they respectively tend to expand and contract radially when rotated in a predetermined rotation direction. This respective tendency of the subcables 66 and 68 to expand and contract radially will therefore create, during rotation of the same in a predetermined rotation direction, an essentially rigid union therebetween so that torque is effectively transferred to the housing 12.

Additional longitudinal stiffness may be provided by means of one or more elongate fiber elements 69a, 69b (see FIG. 3) whose distal ends are embedded within an epoxy layer 70. Preferably, the fibers elements 69a, 69b are each formed of an aromatic polyamide (e.g., Kevlar ® polyamide fiber, E.I.DuPont de Nemours & Co.), but other suitable synthetic fibers may be employed.

Further details of the preferred torque cable 64 which may be employed in the present invention can be obtained from the above-identified commonly owned and copending U.S. application Ser. No. 395,839.

The distal end of the torque cable 64 is rigidly affixed within the proximal end of housing 44 via a suitable electrically conductive epoxy cement, shown generally by reference numeral 70 in FIGS. 2 and 3. The torque cable is therefore electrically coupled to the housing 44 via this electrically conductive epoxy 70. The transducer 26 is thus in electrical communication with the housing 44 (via electrically conductive epoxy 48) and hence with the torque cable 60. One leg of a series connection between the microcoax cable 28 and the transducer 26 is effected by bringing portions 28a, 28b of the outer (shielding) conductor of the microcoax cable 28 into electrical contact with the interior of the torque cable 64 as shown particularly in FIG. 2. While these portions 28a and 28b can, if desired, be soldered to the interior of the torque cable 64, it is presently preferred to maintain their electrical contact via an elastomeric O-ring 72.

Figure 6:
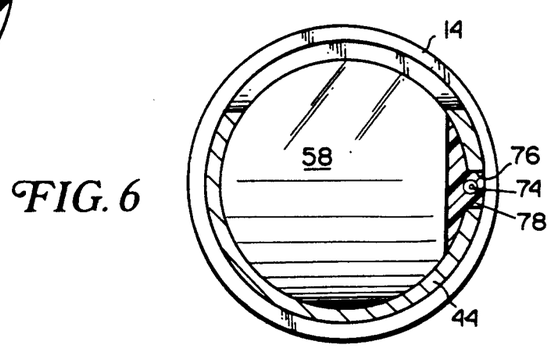
FIG. 6 is a latitudinal cross-sectional view of the probe assembly distal end as taken along line 6—6 in FIG. 2.
Figure 7:
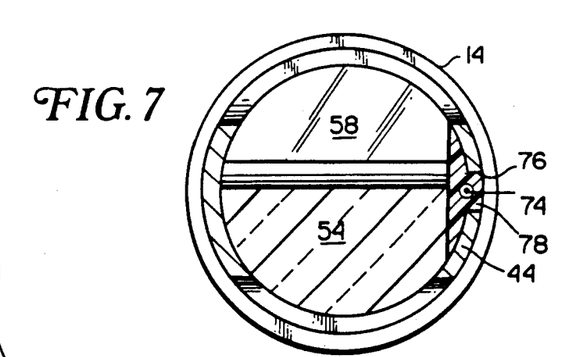
FIG. 7 is a latitudinal cross-sectional view of the probe assembly distal end as taken along line 7—7 in FIG. 2.

The inner conductor 28c is, on the other hand, connected (e.g., via soldering) to a proximal end 74a of an electrically insulated wire 74, the major extent of which is embedded within the wall of the housing 44 (see FIG. 3). As is shown in greater detail in FIGS. 4, 6 and 7, a longitudinal channel section 76 is formed in the housing 44. The major length of the wire 74 is placed in the formed channel 76 and is retained therewithin via an electrically conductive epoxy 78. The electrically conductive epoxy 78 moreover serves to reestablish electrical continuity to the housing 44 (which would otherwise not be present due to the interruption via channel 76) and thereby maintains the electrical shielding capabilities of housing 44 (since the outer shield conductor of the microcoax cable 28 is electrically coupled thereto as described above).

The distal end 74b of wire 74 is routed and electrically coupled (e.g., via soldering) to the distal recessed face of transducer 26 and is positionally held via a suitable backing compound 79, for example, an epoxy compound having a dense powder material (tungsten) to increase its acoustic impedance properties and/or to cause scattering of acoustic energy.

Figure 8:
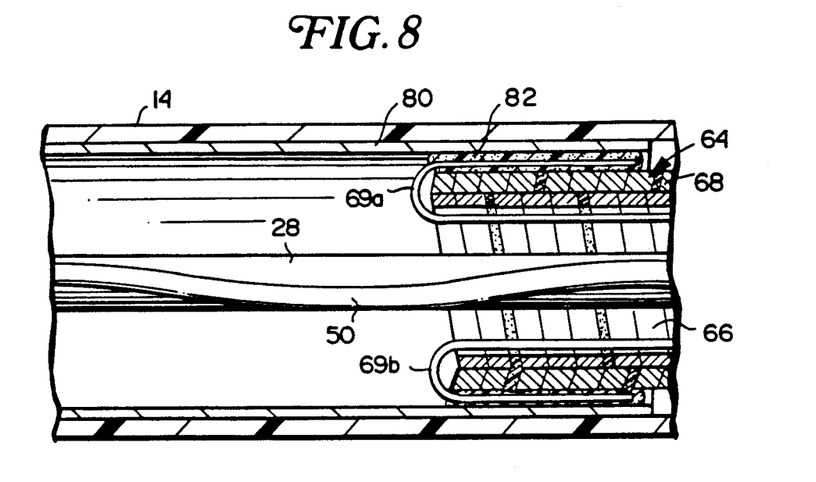
FIG. 8 is a longitudinal cross-sectional view showing the proximal end of the probe assembly of this invention.

As shown in FIG. 8, the proximal end of the torque cable 64 is rigidly affixed to an interior surface of the distal end of an essentially rigid tubular drive shaft 80 (which is preferably fabricated from a conventional stainless steel hypodermic tube) via an epoxy cement 82. The microcoax cable 28 and optical fiber 50 extend through the interior of the drive shaft 80 to the dual function electrical/optical connector 40 as described previously. The proximal ends of the longitudinal stiffening fibers 69a, 69b, moreover are also rigidly affixed within the epoxy cement 82 in an essentially mirror image to the fibers' distal ends.

Figure 9:
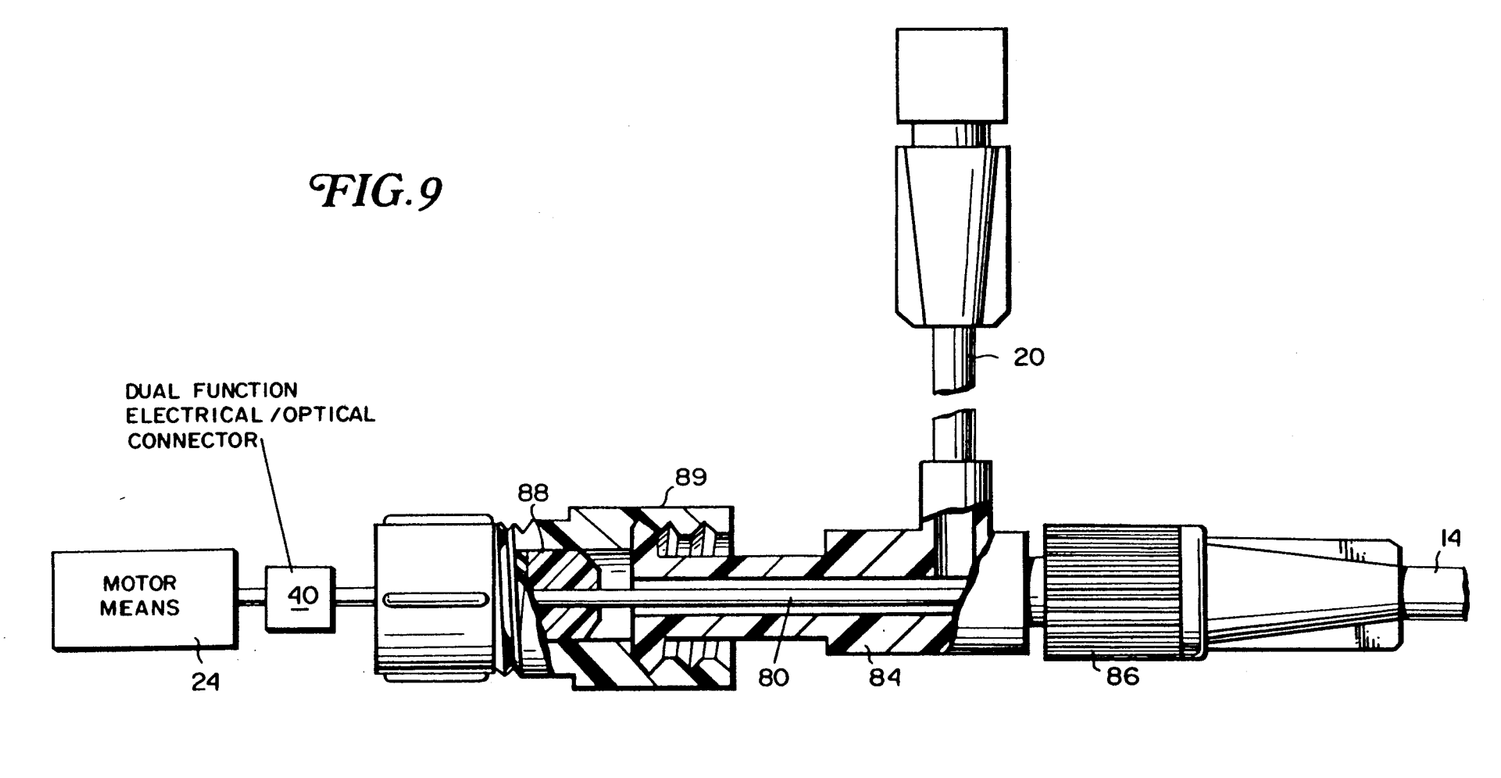
FIG. 9 is a side view (partially sectioned) in a scale smaller than that employed in FIG. 8 showing the proximal structures of the probe assembly of this invention which are located externally of the patient during use.

The proximal end of the probe assembly 11 according to this invention is shown more clearly in accompanying FIG. 9 as including a conventional connector 84 having a sidearm 20 through which a saline solution, for example, may be injected into the lumen 14a of guide catheter 14. The connector and guide catheter 14 are coupled together via a conventional Leur lock 86. The drive shaft 80 coaxially extends through the connector 84 and is operatively coupled to the motor means 24 so as to be capable of being rotatably driven thereby. A length of the drive shaft 80 is supported and sealed via a synthetic resin bearing element 88 (housed within a proximal coupling 89) which serves as a proximal rotational bearing for the shaft 80 and also serves to seal the proximal end of the connector 84 against saline fluid leakage. As discussed previously, the motor means 24 will impart rotation to the drive shaft 80 in a predetermined rotation direction which, in turn, will be transferred to the housing 12 via the torque cable 64.

In use, the guide catheter 14 may be positioned within the patient's cardiovascular system by telescopically advancing the same over a previously positioned guidewire in the manner described more fully in commonly owned and copending U.S. application Ser. No. 07/395,839. The guide wire may then be withdrawn from the guide catheter's lumen 14a so as to allow the attending physician to insert the probe assembly 11 of this invention. The physician may then perform ultrasonic imaging by rotating the housing 12 using the motor means 24 while the housing 12 remains within the relatively transparent portion 16 of guide catheter 14. In this regard, the guide catheter 14 will provide a distal bearing surface to ensure that essentially coaxial rotation of the housing 12 via-a-vis the guide catheter 14 ensues. The ultrasonic imaging will therefore provide a cross-sectional "map" of a region within the particular vessel under investigation.

Once afflicted tissue within the patient's cardiovascular system has been identified via the ultrasonic imaging, the physician may then longitudinally move the subassembly 12 and guide catheter 14 so that the afflicted tissue is in contact with that portion of the body 50 exposed via the window 62 of housing 44 (the precise positioning of the housing 44 having been determined by the previously obtained ultrasonic image "map"). Thereafter, the physician may operate the laser driver 38 so as to cause laser radiation of sufficient duration and intensity to strike the afflicted tissue within the window 62 thereby ablating the same.

It will be appreciated that the attending physician may manually rotate the housing 12 through essentially 180° and operate the ultrasound transceiver 30 so as to view the results of the laser ablation just performed. Thus, after inspecting the ablated tissue region, via ultrasound imaging, the physician may again rotate the housing through 180° so as to once again position the afflicted tissue into the radial path of laser radiation. In such a manner, repeated laser radiation "shots" may be directed against the afflicted tissue until it has been ablated a satisfactory amount. Thereafter, the physician may move to other afflicted tissue identified in the previously obtained ultrasonic imaging map and repeat the therapeutic procedure discussed above.

Although manual rotation of the housing 12 during laser ablation is presently preferred, it will be appreciated that the present invention could be provided with suitable synchronizing circuitry so as to allow, during continuous rotation of the housing 12, ultrasonic imaging and laser ablation to occur simultaneously. In this regard, the synchronizing circuitry will preferably operate so as to provide an image of the previously treated tissue (i.e., tissue which in a previous 180° rotation of the housing 12 had been subjected to laser ablation). Thus, the physician will be capable of determining in real (or essentially near real) time the effects of the laser ablation therapy.

Those in this art will therefore now appreciate that, while the invention has been described in connection with what is presently considered to be the most practical and preferred embodiment, it is not limited to the disclosed embodiment, but on the contrary, is intended to cover various modifications and equivalent arrangements included within the spirit and scope of the appended claims.

What is claimed is:

1. An intravascular probe assembly comprising:

a distally located housing;

optical fiber means having an end terminating within said housing for directing a beam of light along a first path generally parallel to a longitudinal axis of said housing;

ultrasonic transducer means disposed within said housing for generating ultrasonic acoustic waves and for propagating said generated acoustic waves along a second path generally parallel to said housing longitudinal axis;

means disposed in said first and second paths for redirecting said light beam and said acoustic waves from said first and second paths to respective redirected paths generally radially of said housing, and electrical connection means for electrically connecting said transducer means in series, said electrical connection means including;

(i) means for establishing electrical connection between an outer periphery of said ultrasonic transducer means and said housing;

(ii) two-lead cable means having a terminal end located within a proximal portion of said housing;

(iii) a longitudinally extending channel defined in said housing and extending from a proximal location adjacent said terminal end of said two-lead cable means to a distal location adjacent a distal face of said transducer means;

(iv) an electrically insulated wire disposed in said defined channel and having exposed proximal and distal ends at said proximal and distal locations of said defined channel, respectively;

(v) an electrically conductive filler material which fills said channel and retains said wire therewithin;

(vi) one of said leads of said two-lead cable means being electrically connected to said exposed proximal end of said wire at said proximal location of said channel; wherein (vii) said exposed distal end of said wire at said distal location of said channel is electrically connected to a distal face of said transducer means; and wherein (viii) another lead of said two-lead cable means is electrically connected to a proximal region of said housing, whereby said transducer means is series connected.

2. An intravascular probe as in claim 1, wherein said end of said optical fiber means terminates at a proximal location of said housing so as to direct said light beam in a distal direction, and said ultrasonic transducer means is positioned at a distal location of said housing so as to direct said acoustic waves in a proximal direction, and wherein said means for redirecting is disposed between said optical fiber end and said ultrasonic transducer means for redirecting said light beam and said acoustic waves along respective opposite paths generally radially of said housing.

3. An intravascular probe as in claim 1 or 2, further comprising means for positionally maintaining said optical fiber end relative to said housing longitudinal axis.

4. An intravascular probe as in claim 3, wherein said means for positionally maintaining includes a cylindrical ferrule coaxially fixed within said housing, said ferrule holding said optical fiber end essentially coaxial with said housing longitudinal axis.

5. An intravascular probe as in claim 4, wherein said means for redirecting includes a body formed of an optically transparent material, and an optical and acoustic reflecting surface angularly disposed relative to said housing longitudinal axis for redirecting said light beam and said acoustic waves generally radially of said housing.

6. An intravascular probe as in claim 5, wherein said housing defines an open longitudinal trough disposed relative to said reflecting surface to allow said radially redirected acoustic waves to pass therethrough.

7. An intravascular probe as in claim 6, wherein said housing also defines an open circumferential window disposed relative to said reflecting surface to allow said radially redirected light beam to pass therethrough.

8. An intravascular probe as in claim 4, wherein said body includes an essentially planar proximal face, and wherein said ferrule defines an essentially planar distal face separated from said body proximal face to define a space therebetween, and wherein said space is filled with a refractive index matching fluid.

9. An intravascular probe as in claim 1, further comprising electrically conductive torque cable means for transferring rotational motion to said housing, and means for affixing a distal end of said torque cable means within said housing and for establishing electrical communication therebetween, and wherein said another lead of said two-lead cable means is electrically connected to said torque cable distal end, thereby also being electrically connected to said housing proximal region.

10. An intravascular probe assembly comprising:
a distally located electrically conductive housing of preselected length defining a longitudinal axis;
ultrasonic transducer means fixed within said housing so as to be in electrical communication therewith;
said housing defining a channel extending a predetermined extent of said housing length;
an electrically insulated wire positioned within said defined channel and having exposed proximal and distal ends, said exposed distal end being electrically connected to a distal face of said ultrasonic transducer means;
an electrically conductive filler material which fills said channel and retains said wire therewithin;
two-lead cable means for transmitting electrical signals to/from said ultrasonic transducer means, one lead of said two-lead cable means being electrically connected to said exposed proximal end of said wire; and
means for electrically connecting another lead of said two-lead cable means to a proximal region of said housing, whereby said ultrasonic transducer means is electrically connected to said another lead of said two-lead cable means through said electrically conductive housing.

11. An intravascular probe assembly as in claim 10, wherein said two-lead cable means is a coaxial cable, said one lead thereof being a center lead of said coaxial cable, and said another lead thereof being an outer electrically conductive sheath of said coaxial cable.

12. An intravascular probe assembly as in claim 10, further comprising electrically conductive torque cable means for transferring rotation motion to said housing, said torque cable means being rigidly affixed and electrically coupled to a proximal end of said housing.

13. An intravascular probe assembly as in claim 12, wherein said two-lead cable means is positioned within said torque cable means, and wherein said means for electrically connecting includes an elastomeric O-ring which maintains said another lead in electrical contact with said torque cable means.

14. An intravascular probe assembly as in claim 10, wherein said filler material consists essentially of an electrically conductive epoxy.

15. An intravascular probe assembly as in claim 10, further comprising optical fiber means for guiding laser light from an external source thereof to said housing.

16. An intravascular probe assembly as in claim 15, further comprising redirecting means disposed in said housing for redirecting said laser light and acoustic energy produced by said ultrasonic transducer means along respective paths generally radially of said housing.

17. An intravascular probe assembly as in claim 16, wherein said optical fiber means guides said laser light along a first distally directed axial path relative to said housing longitudinal axis, and said ultrasonic transducer means propagates acoustic energy along a second proximally directed axial path relative to said housing, and wherein said redirecting means is disposed between said optical fiber means and said ultrasonic transducer means in said first and second paths.

18. An intravascular probe assembly as in claim 17, wherein said housing means includes means defining an open trough in alignment with said respective generally radial path of said redirected acoustic energy, and means defining an open window in alignment with said respective generally radial path of said redirected laser radiation.

19. An intravascular probe assembly as in claim 18, wherein said redirecting means includes a body consisting essentially of an optically transparent material, and reflective surface means for redirecting incident laser radiation and ultrasonic energy along said respect paths thereof.

20. An ultrasonic medical probe comprising an elongate flexible catheter element, a tubular electrically conductive housing connected at a distal end of said catheter element, an ultrasonic transducer housed within said housing and having an outer periphery thereof electrically connected to said housing, and electrical connection means for electrically connecting said transducer in series, said electrical connection means including:
(i) a two-lead cable having a terminal end located within said housing;
(ii) a longitudinally extending channel defined in said housing and extending from adjacent said terminal end of said two-lead cable to adjacent said transducer;

(iii) an electrically insulated wire disposed in said defined channel and having exposed ends at locations adjacent said terminal end of said two-lead cable and said transducer, respectively;

(iv) an electrically conductive filler material which fills said channel and retains said wire therewithin; wherein (v) one of said leads of said two-lead cable is electrically connected to said one exposed end of said wire, and the other of said exposed ends of said wire is electrically connected to a distal face of said transducer; and wherein (vi) another of said leads of said two-lead cable is electrically connected to a region of said housing, whereby said transducer is series connected.

21. A probe as in claim 20, further comprising a tubular wound wire element extending the length of said flexible catheter and having a distal end connected to a proximal end of said housing.

22. A probe as in claim 21, wherein said wound wire element is electrically connected to said housing, and wherein said probe includes an elastomer O-ring for maintaining said another lead in electrical contact with said wound wire element.

23. A probe as in claim 20, wherein said filler includes an electrically conductive epoxy.

24. A probe as in claim 20, wherein said two-lead cable is a coaxial cable, said one lead thereof being a center lead of said coaxial cable, and said another lead thereof being an outer electrically conductive sheath of said coaxial cable.

* * * * *